United States Patent [19]
Wu et al.

[11] Patent Number: 5,981,547
[45] Date of Patent: Nov. 9, 1999

[54] HOMOCHROMAN DERIVATIVES AND RELATED COMPOUNDS USEFUL AS ANTI-INFLAMMATORY AGENTS

[75] Inventors: Laurence Ichih Wu, Cincinnati; John Michael Janusz, West Chester, both of Ohio

[73] Assignee: The Procter & Gamble Company, Cincinnati, Ohio

[21] Appl. No.: 09/057,686

[22] Filed: Apr. 9, 1998

Related U.S. Application Data

[62] Division of application No. 08/595,087, Feb. 1, 1996, Pat. No. 5,821,250.

[51] Int. Cl.⁶ ............... A61K 31/33; A61K 31/38; C07D 407/04; C07D 409/04
[52] U.S. Cl. ............... 514/300; 514/364; 514/368; 514/370; 514/431; 514/450; 546/121; 548/131; 548/154; 548/193; 548/203; 549/9; 549/355
[58] Field of Search ............... 549/9, 355; 546/121; 548/131, 154, 193, 203; 514/368, 364, 370, 300, 431, 450

[56] References Cited

PUBLICATIONS

Chem. Abstract (I), A New Heterocyclic Sulfur cpd., homo–thiachroman, 1669 h, vol. 41: Abstract of Cagniant et. al., Compt. Rend, vol. 223, pp. 677–679 (1946), 1947.

Chem. Abstract II, A New Heterocyclic cpd; homochroman, vol. 44, 4470 f: Abstract of Cagniant, Compt. Rend, vol. 229, pp. 889–891 (1949), 1950.

*Primary Examiner*—Bernard Dentz
*Attorney, Agent, or Firm*—Carl J. Roof; Mary Pat McMahon; David L. Suter

[57] ABSTRACT

A compound having the structure:

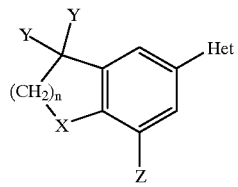

wherein (a) n is from about 1 to about 3;

(b) X is selected from the group consisting of O, S, SO, or $SO_2$;

(c) Y is independently hydrogen or straight, branched or cyclic alkyl having from 1 to about 4 carbon atoms, or the Y's are bonded together to form an alkanyl ring having from about 3 to about 7 atoms;

(d) Z is hydrogen or straight, branched or cyclic alkyl having from 3 to about 10 atoms other than hydrogen; and (e) Het is a heteroaryl group comprising one or more rings each ring containing from about 5 to about 6 atoms other than hydrogen and wherein the group contains at least one heteroatom selected from O, N, or S.

pharmaceutical compositions comprising such compounds, and methods of treating inflammation or pain using such compounds.

13 Claims, No Drawings

HOMOCHROMAN DERIVATIVES AND RELATED COMPOUNDS USEFUL AS ANTI-INFLAMMATORY AGENTS

This is a divisional of U.S. Ser. No. 08/595,087, filed Feb. 1, 1996, now U.S. Pat. No. 5,821,250.

TECHNICAL FIELD

The subject invention relates to nonsteroidal anti-inflammatory drugs, particularly to substituted dihydrobenzpfuran and related compounds.

BACKGROUND OF THE INVENTION

Certain dihydrobenzofuran compounds and other compounds structurally related thereto have been found to have significant disease altering activities. Such compounds, processes for making them, and uses for them are disclosed in the following references: U.S. Pat. No. 4,670,457 issued to Doria, Romeo & Como on Jun. 2, 1987; U.S. Pat. No. 4,849,428 issued to Dobson, Loomans, Matthews & Miller on Jul. 18, 1989; Japanese Patent Publication No. 53-005178 of Yoshitomi Pharm. Ind. KK published Jan. 1, 1978; Hammond, M. L., I. E. Kopka, R. A. Zambias, C. G. Caldwell, J. Boger, F. Baker, T. Bach, S. Luell & D. E. MacIntyre, "2,3-Dihydro-5-benzofuranols as Antioxidant-Based Inhibitiors of Leukotriene Biosynthesis", *J. Med. Chem.*, Vol. 32 (1989), pp. 1006–1020; Ortiz de Montellano, P. R & M. A. Correia, "Suicidal Destruction of Cytochrome P-450 during Oxidative Drug Metabolism", *Ann. Rev. Pharmacol. Toxicol.*, Vol. 23 (1983), pp. 481–503; Chakrabarti, J. K., R. J. Eggleton, P. T. Gallagher, J. Harvey, T. A. Hicks, E. A. Kitchen, and C. W. Smith, "5-Acyl-3-substituted-benzofuran-2-(3H)-ones as Potential Anti-inflammatory Agents", *J. Med. Chem.*, Vol. 30 (1987), pp 1683–1688.

It is an object of the subject invention to provide compounds which have effective anti-inflammatory, analgesic and/or anti-oxidant activity.

It is a further object of the subject invention to provide such compounds which cause few adverse side effects.

It is also an object of the subject invention to provide methods for treating inflammation and/or pain using the subject compounds.

SUMMARY OF THE INVENTION

The subject invention compounds having the structure:

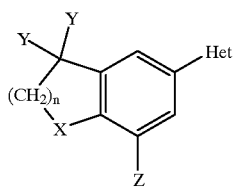

wherein
- (a) n is from 1 to about 3;
- (b) X is selected from the group consisting of O, S, SO, or $SO_2$;
- (c) Y is independently hydrogen or straight, branched or cyclic alkyl having from 1 to about 4 carbon atoms, or the Y's are bonded together to from an alkanyl ring having from about 3 to about 7 atoms;
- (d) Z is hydrogen or straight, branched or cyclic alkyl having from 3 to about 10 atoms other than hydrogen; and
- (e) Het is a heteroaryl group comprising one or more rings each ring containing from about 5 to about 6 atoms other than hydrogen and wherein the group contains at least one heteroatom selected from O, N, or S.

DETAILED DESCRIPTION OF THE INVENTION

As used herein, unless otherwise indicated, "alkyl" or "alkanyl" means a straight, branched or cyclic hydrocarbon chain, saturated or unsaturated, unsubstituted or substituted. Perferred alkyl are $C_1$–$C_{10}$; more preferred are $C_1$–$C_8$; especially preferred are $C_1$–$C_4$. Preferred alkyl are straight chain. Preferred branched alkyl having one or two branches, preferably one branch. Preferred cyclic alkyl are monocyclic or are a straight chain with a monocyclic terminus. Preferred alkyl are saturated. Preferred alkyls are unsubstituted. Preferred substituted alkyl are mono-, di-, or trisubstituted, more preferably monosubstituted. Preferred alkyl substituents include halo, hydroxy, oxo, alkoxy (e.g., methoxy, ethoxy, propoxy, butoxy, pentoxy), aryloxy (e.g., phenoxy, chlorophenoxy, tolyloxy, methoxyphenoxy, benzyloxyphenoxy, alkyloxycarbonylphenoxy, acyloxyphenoxy), acyloxy(e.g., propionyloxy, benzoloxy, acetoxy), carbamoyloxy, carboxy, mercapto, alkythio, acylthio, aryltio (e.g., phenylthio, chlorophenylthio, alkylphenylthio, alkoxyphenylthio, benzylthio, alkyloxycarbonylphenylthio), aryl (e.g., phenyl, toyl, alkyloxphenyl, alkyloxycarbonylphenyl, halophenyl), heterocyclyl (e.g. piperidinyl, tetrahydrothienyl, pyrrolidinyl, piperazinyl, morpholinyl, thiomorpholinyl, tetrahydropyranyl, tetrahydrothiopyranyl, tetrahydrofuranyl, imidazolidinyl, pyrazolidinyl, oxazolidinyl, isoxazolidinyl, thiazolidinyl, isothiazolidinyl, azepinyl, oxepinyl, thiepinyl, triazolidinyl, tetrazolidinyl), heteroaryl, amino (e.g., amino, mono- and di- $C_1$–$C_3$ alkanylamino, methylphenylamino, methylbenzylamino), $C_1$–$C_3$ alkanylamido, ureido, N'-alkylureido, N',N'-dialkylureido, N',N',N-trialkylureido, guanidino, N'-alkylguanidino, N',N''-dialkylguanidino, or alkoxy carbonyl.

As used herein, "alkoxy" means —O-alkyl.

As used herein, "aryl" means a moiety having an unsubstituted or substituted aromatic ring having 6 to about 10 carbon atoms. Preferred aryl are phenyl and naphthyl; most preferred aryl is phenyl. Preferred aryl are unsubstituted. Preferred substituted aryl are mono-, di-, or trisubstituted, more preferably monosubstituted. Preferred aryl substituents include hydroxy, mercapto, halo, methyl, ethyl and propyl.

As used herein, "halo" means fluro, chloro, bromo or iodo. Preferred halo are fluoro, chloro and bromo; more preferred are chloro and bromo, especially chloro.

As used herein, "heteroaryl" means a moiety having at least 1 heteroatom, one or more rings each ring having from 1 to 6 carbon atoms and a total of from 1 to 6 heteroatoms selected from O, S, and N. Preferred heteroaryl groups include 1 to 3 heteroatoms in the ring. Specific preferred heterocycles include 2 or 3-furyl, 2 or 3-thienyl, 2 or 3-pyrrolyl either unsubstituted or alkyl substituted on nitrogen, 2, 4, or 5 thiazolyl, 2 or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, imidazothiazolinyl, imidazopyridinyl, imidazoimidazolinyl, indolyl, quinolyl, isoquinolyl. Heteroaryl groups are unsubstituted or substituted, preferably unsubstituted. Preferred substituted heteroaryls are mono-, di-, or trisubstituted, more preferably monosubstituted. Preferred substitutents include alkyl, halo, hydroxy, alkoxy, thio, nitro, amino, amido, ureido, guanidino, thiocarbamamido, thioureido.

Compounds

The subject invention involves compounds having the following structure;

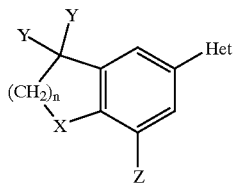

4 wherein (a) n is from about 1 to about 3;

(b) X is selected from the group consisting of O, S, SO, or $SO_2$;

(c) Y is independently hydrogen or straight, branched or cyclic alkyl having from 1 to about 4 carbon atoms, or the Y's are bonded together to form an alkanyl ring having from about 3 to about 7 atoms;

(d) Z is hydrogen or straight, branched or cyclic alkyl having from 3 to about 10 atoms other than hydrogen; and (e) Het is a heteroaryl group comprising one or more rings each ring containing from about 5 to about 6 atoms and wherein the group contains at least one heteroatom selected from O, N, or S.

In the above structure, each Y is independently selected from hydrogen, straight or branched alkanyl having from 1 to about 4 carbon atoms, and cyclic alkyl having about 3 carbon atoms, cyclopropyl, or the Y's are bonded together to from an unsubstituted cyclic alkanyl ring having from 3 to about 7 carbon atoms in the ring. Each Y is preferably hydrogen, methyl, ethyl or cyclopropyl; more preferably hydrogen or methyl; most preferably methyl. Preferably both Y's are the same. When the Y's are bonded together to form a cyclic ring, the ring is preferably cyclopropyl, cyclobutyl or cyclopentyl, more preferably cyclopropyl.

In the above structure, Z is selected from hydrogen or branched or cyclic alkyl, and unsubstituted or alkanyl-substituted phenyl, or benzyl. When Z is not hydrogen, Z preferably has from 3 to about 10 atoms other than hydrogen. Z is preferably saturated. Z is preferably branched alkanyl having from about 3 to about 8 carbon atoms, more preferably from about 4 to about 6 carbon atoms. Z is preferably branched alkanyl having 2 or more branches, more preferably 2 branches. Preferred branched alkanyl Z include t-butyl, neopentyl, isopropyl; most preferred is t-butyl. Preferred cyclic alkanyl Z include cyclopropyl, cyclobutyl, cyclopentyl, cyclohexyl, cycloheptyl. Also preferred cyclic alkanyl Z include methyl or ethyl with a terminal cyclopropyl, cyclobutyl or cyclopentyl, especially cyclopropylmethyl or cyclopropylethyl. Also preferred Z is unsubstituted phenyl or benzyl.

In the above structure, Het is selected from the group consisting of 2 or 3-furyl, 2 or 2-thienyl, 2 or 3-pyrrolyl either unsubstituted or alkyl substituted on nitrogen, 2, 4, or 5 thiazolyl, 2 or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxdiazolyl, 2 or 5-thiadiazolyl, triazolyl, tetrazolyl, pyridyl, pyrimidinyl, pyrazinyl, imidazothiazolinyl, imidazopyridinyl, imidazoimidazolinyl, indolyl, quinolyl, isoquinolyl.

Preferred compounds of the subject invention are included in the following table:

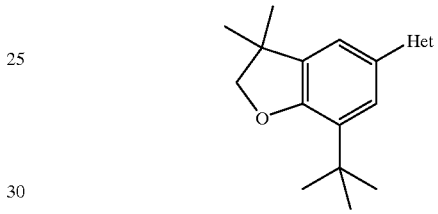

| Compound No. | Het |
|---|---|
| 1 | 2-furanyl |
| 2 | 2-thienyl |
| 3 | 2-(5-bromothienyl) |
| 4 | 4-thiazolyl |
| 5 | 4-(2-guanidinothiazolyl) |
| 6 | 5-methyl-1,2,4-oxadizolyl |
| 7 | 6-imidazo[2,1,b]thiazolinyl |
| 8 | 1-oxo-6-imidazo[2,1,b]thiazolinyl |
| 9. | 2-imidazo(1,2a)pyridine |

In order to determine and assess pharmacological activity, testing of the subject compounds in animals is carried out using various assays known to those skilled in the art. The anti-inflammatory activity of the subject compounds can be conveniently demonstrated using an assay designed to test the ability of the subject compounds to antagonize the local edema which is characteristic of the inflammatory response. Examples of such known tests include the rat carrageenan edema test, the oxazolone-induced inflamed mouse ear test, and the mouse arachadonic acid-induced inflamed ear test. Analgestic activity may be tested in art-known models such as the phenylbenzoquinone-induced writhing test in mice, and the Randall & Selitto test in rats. Another useful art-known test is the rat adjuvant arthritis test which is a useful model for assessing anti-inflammatory activity, anti-arthritic and anti-resorptive activity in a chronic, rather than an acute, model.

These and other appropriate tests for phamacological activity are disclosed and/or referred to in U.S. Pat. No. 4,130,666 issued to Moore on Dec. 19, 1978; U.S. Pat. No. 4,431,656 issued Feb. 14, 1984 to Katsumi, et al.; U.S. Pat. No. 4,440,784 issued to Katsumi, et al. on Apr. 3, 1984; Japanese Patent Application 85/54315 of Katsumi, et al., published Mar. 28, 1985; European Patent Application No.

0,059,090 of Yamanuchi Pharmaceutical Company Ltd., published Sep. 1, 1982; Opas, E. V., R. J. Bonney & J. L. Humes, "Postaglandin and Leukotriene Systhesis in Mouse Ears Inflamed by Arachadonic Acid", *The Journal of Investigative Dermatology*, Vol. 84, No. 4 (1985), pp. 253–256; Swingle, K. F., R. L. Bell & G. G. I. Moore, "Anti-inflammatory Activity of Antioxidants", *Anti-inflammatory and Antirheumatic Drugs*, Vol. III, Chapter 4, K. D. Rainsford, ed., CRC Press, Inc., (1985), pp. 105–126; Adamkiewicz, V. W., W. B. Rice & J. D. McColl, "Antiphlogistic Effect of Trypsin in Normal and in Adrenalectomized Rats", *Canadian Journal of Biochemistry & Physiology*, Vol. 33 (1955), pp. 332–339; Sellye, H., "Further Studies Concerning the Participation of the Adrenal Cortex in the Pathogenesis of Arthritis", *British Medial Journal*, Vol. 2 (1949), pp. 1129–1135; and Winter, C. A., E. A. Risley & G. W. Nuss, "Carrageenan-Induced Edema in Hind Paw of the Rats as an Assay for Antiinflammatory Drugs" *Proceedings of Society of Experimental Biology and Medicine*, Vol. 111 (1962), pp. 544–547; Otterness, I.,& M. L. Bliven, "Laboratory Methods for Testing Nonsteroidal Antiinflammatory Drugs", *Nonsteroidal Antiinflammatory Drugs*, Chapter 3, J. G. Lombardion, ed., John Wiley & Sons, Inc. (1985), pp. 111–252. Hitchens, J. T., S. Goldstein, L. Shernano & J. M. Beiler, "Analgesic Effects of Irritants in Three Models of Experimentally-Induced Pain", *Arch. Int. Pharmacodyn.*, Vol. 169, No. 2 (1967) pp. 384–383; Milne, G. M. & T. M. Twomey, "The Analgetic Properties of Piroxicam in Animals and Correlation with Experimentally Determined Plasma Levels", *Agents and Actions*, Vol. 111, No. 1/2 (1960), pp. 31–37; Randall, L. O. & J. J. Selitto, "A Method for Measurement of Analgesic Activity on Inflamed Tissue", *Arch. Int. Pharmacodyn.*, Vol. 111, No. 4 (1957), pp. 409–419; Winter, C. A. & L. Faltaker, "Nociceptive Thresholds as Affected by Parenteral Administration of Irritants and of Various Antinociceptive Drugs", *J. Pharmacol. Exp. Ther.*, Vol. 148, No. 3 (1965), pp. 373–379; the disclosure of all these references are incorporated herein by reference, Many anti-inflammatory drugs, particularly non-steroidal anti-inflammatory drugs (NSAIDs) cause undesirable gastrointestinal side effects, especially when dosed perorally; such side effects may include ulcers and erosins. These side effects, which are often asymptomatic, can become serious enough to require hospitalization and can even be lethal. Compounds of the subject invention generally cause fewer such gastrointestinal side effects compared to other NSAIDs. Some compounds of the subject invention are even gastroprotective, protecting the stomach and intestines from ulcers and erosions, particularly those caused by ethanol or other NSAIDs.

Certain NSAIDs, when dosed systematically, cause an undesirable increase in systemic levels of certain liver enzymes. Compounds of the subject invention generally cause little or no liver enzyme side effects.

Compounds useful in the subject invention can be made using the following general reaction schemes:

The furanyl and thienyl substituted dihydrobenzofurans (DHBF) can be prepared by palladium(O)-mediated Stille coupling reactions (Zimmerman, E. K.; Stille, J. K. *Macromolecules* 1985, 18, 321) between 5-bromo derivative of DHBF and 2-(tributylstannyl)furan or 2-(tributylstannyl) thiophene. Further reactions of the 2-thiophene compound by Friedel-Crafts acylation and bromination afford the acyl and bromo derivatives respectively.

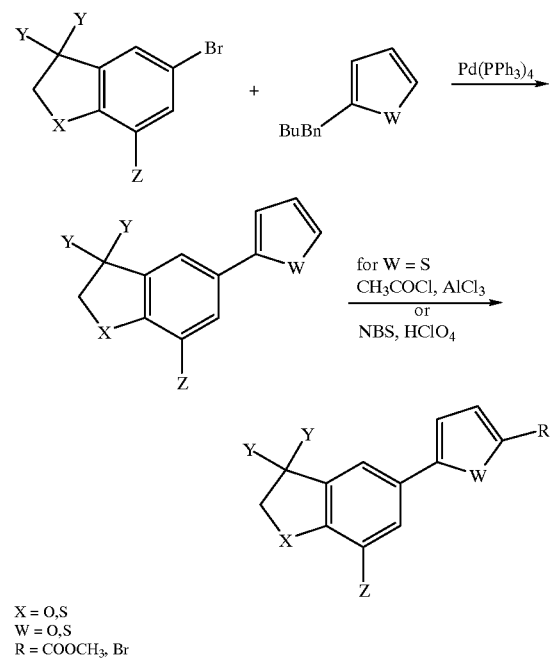

X = O,S
W = O,S
R = COOCH$_3$, Br

The thiazoles, imidazothiazolines and the imidazopyridine are prepared from the 5-haloacetyl derivative of the DHBF. The 5-bromoacetyl derivative of the DHBF is synthesized from the 5-acetyl derivative by reaction of the corresponding trimethylsilyl enol ether (LDA, TMSCI) with NBS; the preparation of the 5-chloroacetyl derivative of DHBF is accomplished by reaction of the 5-acetyl derivative of the DHBF with benzyltrimethylammonium dichloroiodate (Kajigaeshi, S.; Kakinami, T.; Morlwaki, M.; Fujisaki, S.; Maeno, K.; Okamoto, T. *Synthesis* 1988, 545). Reaction of the bromoacetyl compound with 2-amino-2-thiazoline gives the imidazothiazoline which is oxidized with m-chloroperbenzoic acid to the sulfinyl derivative. Reaction of the bromoacetyl compound with 2-iminobluret or ethyl thiooxamide provides the 2-substituted thiazole derivatives. The unsubstituted thiazole is prepared by hydrolysis of the 2-carboethoxy derivative followed by decarboxylation. The imidazopyridine is prepared by condensation of 2-aminopyridine with the chloroacetyl DHBF derivative.

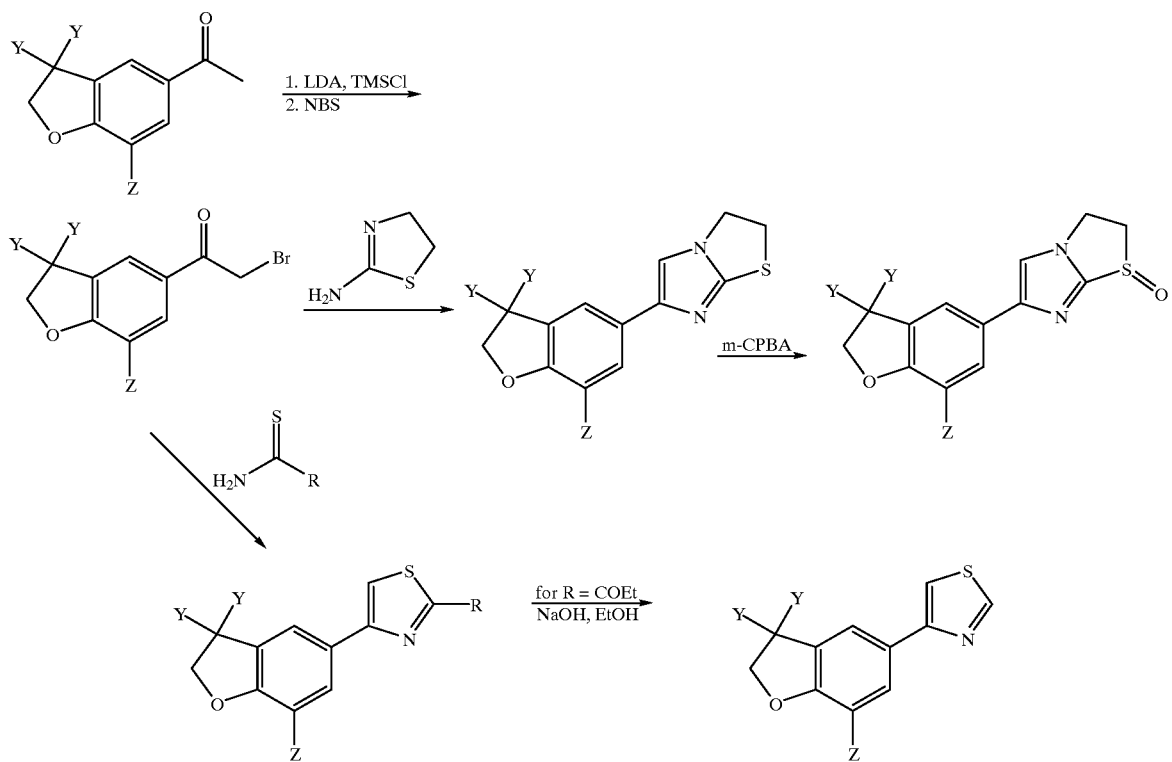
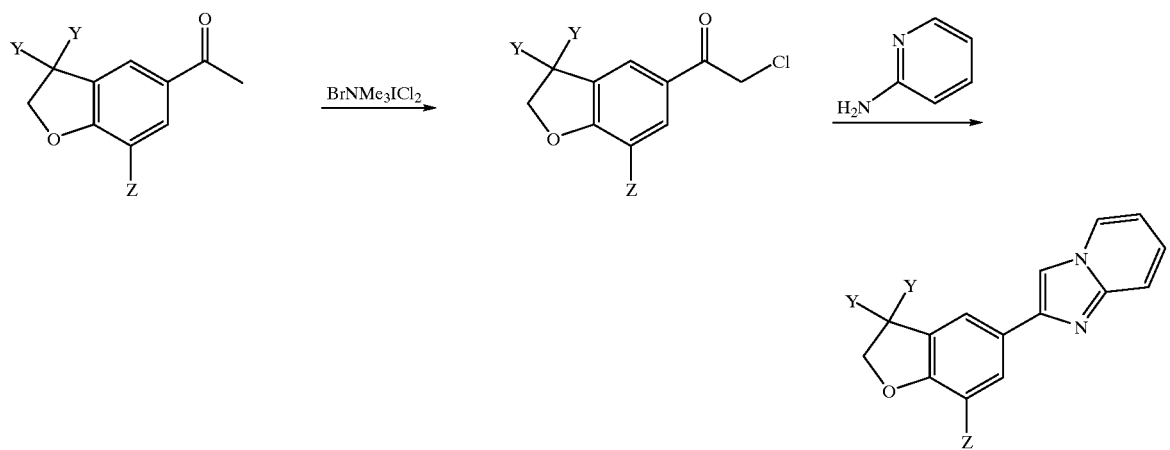
The oxidiazole is prepared by condensation between acetyl chloride and the N-hydroxy amidine of the DHBF structure in pyridine. The N-hydroxy amidine compound is prepared from the cyano derivative by reaction with hydroxylamine hydrochloride in the presence of potassium carbonate.
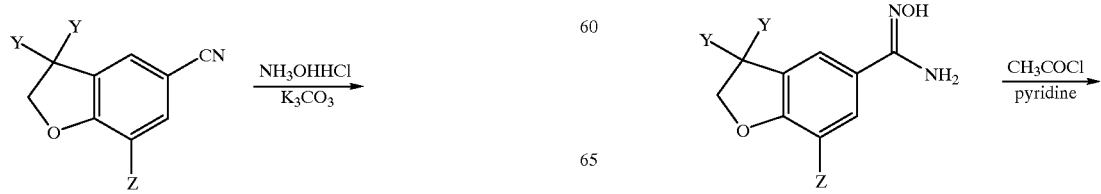

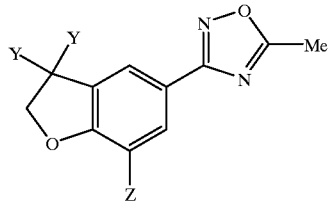

Synthesis Examples

The following non-limiting examples provide further information regarding synthesis of the subject compounds.

EXAMPLE 1

7-tert-Butyl-2,3-dihydro-3,3-dimethyl-5-(2-furanyl) benzo[b]furan

A mixture of 5-bromo-7-tert-butyl-2,3-dihydro-3,3-dimethylbenzo[b]furan (1.13 g, 4.0 mmol), 2-(tributylstannyl)furan (1.71 g, 4.8 mmol), tetrakis(triphenylphosphine)palladium (0.46 g, 0.4 mmol), and 20 mL of toluene is heated under argon at reflux of 30 min. The reaction mixture is cooled to room temperature, concentrated in vacuo, diluted with ether, washed with 10% aqueous ammonium hydroxide solution and with brine, dried over anhydrous magnesium sulfate, and concentrated to give a dark oil. Purification by flash column chromatography on silica gel (1% ethyl acetate-hexane) yields about 0.47 g (43%) of the title compound as a light yellow oil.

EXAMPLE 2

7-tert-Butyl-2,3-dihydro-3,3-dimethyl-5-(2-thienyl) benzo[b]furan

A mixture of 5-bromo-7-tert-butyl-2,3-dihydro-3,3-dimethylbenzo[b]furan (2.26 g, 8.0 mmol), 2-(tributylstannyl)thiophene (3.05 mL, 9.6 mmol), tetrakis(triphenylphosphine)palladium (0.92 g, 0.8 mmol), and 40 mL of toluene is heated under argon at reflux of 2 h. The reaction mixture is cooled to room temperature, diluted with ether, washed with 10% aqueous ammonium hydroxide solution and with brine, dried over anhydrous magnesium sulfate, and concentrated in vacuo to give 6.44 g of a dark oil. Purification by flash column chromatography on silica gel (0.5% ethyl acetate-hexane) yields about 0.98 g (45%) of the title compound initially as a colorless oil, which solidifies upon standing; mp 61–63° C.

EXAMPLE 3

5-[2-(5-Bromothienyl)]-7-tert-butyl-2,3-dihydro-3,3-dimethylbenzo[b]furan

To a solution of 7-tert-butyl-2,3-dihydro-3,3-dimethyl-5-thienylbenzo[b]furan (0.88 g, 3.0 mmol) in 30 mL of hexane there is added N-bromosuccinimide (0.51 g, 2.85 mmol) and 70% perchloric acid (10 mL). The resulting suspension is stirred for 1 h, filtered through Celite, and concentrated in vacuo to give a dark viscous oil. Purification by flash column chromatography on silica gel(0.5% ethyl acetate-hexane) yields about 0.60 g (55%) of the title compound as a colorless solid: mp 89–90° C.

EXAMPLE 4

4-[5-(7-tert-Butyl-2,3-dihydro-3,3-dimethylbenzo[b] furanyl)]thiazole Step 1: 4-[5-(7-tert-Butyl-2,3-dihydro-3,3-dimethylbenzo[b]furanyl)]-2-(ethoxycarbonyl)thiazole A mixture of 5-bromoacetyl-7-tert-butyl-2,3-dihydro-3,3-dimethylbenzo[b]furan (3.58 g, 11.0 mmol) and ethyl thiooxamate (1.60 g, 12.0 mmol), and 60 mL of ethanol is heated at reflux for 2 h. The reaction mixture is cooled to room temperature and concentrated in vacuo. The solid residue is dissolved in dichloromethane; this solution is washed with aqueous sodium bicarbonate solution and with water, then dried over anhydrous magnesium sulfate, and concentrated in vacuo to yield about 4.56 g of the crude product. Purification by flash column chromatography on silica gel (8% ethyl acetate-hexane) gives about 3.52 g (89%) of the title compound as a colorless solid: mp 125–126° C.

4-[5-(7-tert-Butyl-2,3-dihydro-3,3-dimethylbenzo[b] furanyl)]thiazole

A mixture of 4-[5-(7-tert-butyl-2,3-dihydro-3,3-dimethylbenzo[b]furanyl)]-2-(ethoxycarbonyl)thiazole (2.80 g, 7.8 mmol), sodium hydroxide (0.6 g, 15.0 mmol), and 30 mL of ethanol is heated at reflux of 0.5 h. The reaction mixture is cooled to room temperature and concentrated to give 2.16 g of the crude product. Purification by flash column chromatrography on silica gel (10% ethyl acetate-hexane) affords about 0.80 g (36%) of the title compound as a light yellow solid: mp 100–101° C.

EXAMPLE 5

4-[5-(7-tert-Butyl-2,3-dihydro-3,3-dimethylbenzo[b] furanyl)]-2-guanidinothiazole A mixture of 5-bromoacetyl-7-tert-butyl-2,3-dihydro-3,3-dimethylbenzo[b]furan (0.66 g, 2.0 mmol), 2-iminothiobiuret (0.24 g, 2.0 mmol), and 10 mL of acetone is heated at reflux for 24 h. The reaction mixture is cooled to room temperature and concentrated in vacuo. The residue is dissolved in 1:1 ethyl acetate-THF mixture, and this solution is washed with aqueous potassium carbonate solution. The organic layer is dried over anhydrous magnesium sulfate and concentrated in vacuo. Purification of the residue by flash column chromatography on silica gel (5% methanol-chloroform) affords about 0.24 g (35%) of the title compound as a colorless solid: mp 237–238° C.

EXAMPLE 8

7-tert-Butyl-2,3-dihydro-3,3-dimethyl-5-(5-methyl-1,2,4-oxadiazolyl)benzo[b]-furan Step 1: 7-tert-Butyl-2,3-dihydro-3,3-dimethyl-5-benzo[b] furancarboxamide Oxime A mixture of 7-tert-butyl-5-cyano-2,3-dihydro-3,3-dimethylbenzo[b]-furan (6.39 g, 27.9 mmol), potassium carbonate (15.80 g, 114.0 mmol), hydroxylamine hydrochloride (7.93 g, 114.0 mmol), and 135 mL of ethanol is heated at reflux for 20 h. The reaction mixture is cooled to room temperature, filtered, and concentrated in vacuo to give a solid residue. Purification by flash column chromatography on silica gel (20% ethyl acetate-hexane→5% methanol-dichloromethane) furnishes about 3.13 g (43%) of the title compound as a colorless foamy solid: mp 109–110° C.

Step 2: 7-tert-Butyl-2,3-dihydro-3,3-dimethyl-5-(5-methyl-1,2,4-oxadiazolyl)benzo[b]furan To a solution of 7-tert-butyl-2,3-dihydro-3,3-dimethyl-5-benzo-[b]furancarboxamide oxime (1.05 g. 4.0 mmol) in 20 mL of pyridine is added acetyl chloride (0.43 mL, 6.0 mmol). The reaction mixture is heated at 95° C. for 22 h and cooled to room temperature. Pyridine is removed in vacuo at 50° C.; the residue is partitioned between water and ethyl acetate. The organic layer is washed with water and with brine, dried over anhydrous magnesium sulfate, filtered, and concentrated in vacuo to give 1.33 g of the crude product. Purification by flash column chromatography on silica gel (10% ethyl acetate-hexane) produces about 0.60 g (52%) of the title compound as a colorless solid: mp 81–82° C.

EXAMPLE 7

6-[5-(7-tert-Butyl-2,3-dihydro-3,3-dimethylbenzo[b] furanyl)]imidazo[2,1,b]-thiazoline Step 1: 5-Bromoacetyl-7-tert-butyl-2,3-dihydro-3,3-dimethylbenzo[b]furan A solution of 5-acetyl-7-tert-butyl-2,3-dihydro-3,3-dimethylbenzo[b]furan (2.46 g, 10.0 mmol) in 25 mL of anhydrous THF is added dropwise to lithium diisopropylamide (6.0 mL, 12.0 mmol, 2.0M solution in heptane-THF-ethyl benzene) at −78° C. The resulting solution in stirred at −78° C. for 15 min, and chlorotrimethylsilane (1.5 mL, 12.0 mmol) is introduced. The reaction mixture is stirred at −78° C. for 15 min, warmed to room temperature, stirred for 1.5 h, quenched with water, and extracted with ether. The extract is dried over anhydrous sodium sulfate and concentrated in vacuo; the residue is dissolved in 25 mL of anhydrous THF and reacted at 0° C. with N-bromosuccinimide (1.78 g, 10.0 mmol). The resulting yellowish solution is kept at 0° C. for 0.5 h, warmed to room temperature, stirred for 0.5 h, quenched with water, and extracted with ether. The extract is dried over anhydrous magnesium sulfate and concentrated in vacuo. Purification of the residue by flash column chromatography on silica gel (5%→20% ether-hexane) affords about 2.85 g (88%) of 5-bromoacetyl-7-tert-butyl-2,3-dihydro-3,3-dimethyl-benzo[b]furan as a yellowish solid: mp 54–56° C.

Step 2: 6-[5-(7-tert-Butyl-2,3-dihydro-3,3-dimethylbenzo[b]furanyl)]imidazo[2,1,b]thiazoline A mixture of 5-bromoacetyl-7-tert-butyl-2,3-dihydro-3,3-dimethylbenzo[b]furan (0.81 g, 2.5 mmol) and 2-aminothiazoline (0.25 g, 2.5 mmol), and 10 mL of ethanol is heated at reflux for 20 h. The reaction mixture is cooled to room temperature, concentrated to ca. 5 mL in volume, and poured into water. This solution is adjusted to pH 9 with 20% aqueous potassium carbonate and extracted with ether. The extract is washed with brine, dried over anhydrous magnesium sulfate, and concentrated in vacuo. Purification of the residue by flash column chromatography on silica gel (20% ether-hexane→ether) gives about 0.52 g (63%) of the title compound as a colorless solid: mp 189–190° C.

EXAMPLE 8

6-[5-(7-tert-Butyl-2,3-dihydro-3,3-dimethylbenzo[b] furanyl)]imidazo[2,1,b]-thiazoline 1-Oxide m-Chloroperbenzoic acid (0.82 g, ca. 2.6 mmol, 50–60% pure) is added to a solution of 6-[5-(7-tert-butyl-2,3-dihydro-3,3-dimethylbenzo[b]furanyl)]imidazo[2,1,] thiazoline (0.87 g, 2.6 mmol) in 10 mL of chloroform at 0° C. The reaction is complete within 5 min; the reaction mixture is washed with aqueous sodium bicarbonate solution and with water, dried over anhydrous magnesium sulfate, and concentrated to give a pink solid. Purification by flash column chromatography on silica gel (35% ethyl acetate-hexane→5% methanol-chloroform) yields about 1.0 g of a pinkish solid, which is redissolved in chloroform. Treatment of this solution with hexane results in the precipitation of about 0.67 g (75% of the title compound as a light pink solid: mp 217–219° C.

EXAMPLE 9

2-[5-(7-tert-Butyl-2,3-dihydro-3,3-dimethylbenzo[b] furanyl)]-imidazo(1,2a)pyridine Step 1: 5-Chloroacetyl-7-tert-butyl-2,3-dihydro-3,3-dimethylbenzo[b]furan A mixture of benzyltrimethylammonium dichloroiodate (31.70 g, 91.0 mmol), 5-acetyl-7-tert-butyl-2,3-dihydro-3,3-dimethylbenzo[b]furan (12.35 g, 50.2 mmol), 300 mL of 1,2-dichloroethane, and 120 mL of methanol is heated at reflux for 13 h. The reaction mixture is cooled to room temperature and concentrated in vacuo; 5% aqueous sodium bisulfite solution (125 mL) is added to the residue obtained. This mixture is extracted with ether; the extract is washed with aqueous sodium bicarbonate solution and with brine, dried over anhydrous magnesium sulfate, and concentrated to produce about 14.09 g (100%) of 5-chloro-acetyl-7-tert-butyl-2,3-dihydro-3,3-dimethylbenzo[b]furan as a reddish solid: mp 76–77° C.

Step 2: 2-[5-(7-tert-Butyl-2,3-dihydro-3,3-dimethylbenzo[b]furanyl)]-imidazo-(1,2a)pyridine A mixture of 5-chloroacetyl-7-tert-butyl-2,3-dihydro-3,3-dimethylbenzo[b]furan (1.12 g, 4.0 mmol) and 2-aminopyridine (0.51 g, 5.4 mmol) in 10 mL of ethanol is heated at reflux for 2 h. The reaction mixture is cooled to room temperature and concentrated in vacuo. The residue is dissolved in ethyl acetate; this solution is washed with aqueous sodium carbonate solution and with brine, dried over anhydrous sodium sulfate, and concentrated to furnish about 1.63 g of the crude product. Purification by flash column chromatography on silica gel (20%→25% ethyl acetate-hexane) affords about 0.43 g of a yellow solid, which is washed with hexane to yield 0.42 g (33%) of the title compound as a colorless solid: mp 187–188° C.

EXAMPLE 10

7-tert-Butyl-2,3-dihydro-3,3-dimethyl-5-(2-furanyl) benzo[b]thiophene

A mixture of 5-bromo-7-tert-butyl-2,3-dihydro-3,3-dimethylbenzo[b]thiophene (1.20 g, 4.0 mmol), 2-(tributylstannyl)furan (1.71 g, 4.8 mmol), tetrakis (triphenylphosphine)palladium (0.46 g, 0.4 mmol), and 20 mL of toluene is heated under argon at reflux for 30 min. The reaction mixture is cooled to room temperature, concentrated in vacuo, diluted with ether, washed with 10% aqueous ammonium hydroxide solution and with brine, dried over anhydrous magnesium sulfate, and concentrated to give a dark oil. Purification by flash column chromatography on silica gel (1% ethyl acetate-hexane) yields about 0.46 g (40%) of the title compound as an oil.

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medial judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors with the knowledge and expertise of the attending physician.

Compositions of the subject invention preferably comprise from about 0.1% to about 99.9% by weight of a compound, more preferably from about 20% to about 80%, and most preferably from about 40% to about 70%.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragscanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a subject compound is basically determined by the way the compound is to be administered.

If the subject compound is to be injected, it is preferably injected non-intravenously; the preferred pharmaceutically-acceptable carrier is sterile, physiological saline, with blood compatible suspending agent, the pH of which has been adjusted to about 7.4. Such injectable compositions preferably comprise from about 1% to about 50% of the subject compound, more preferably from about 5% to about 25%, also preferably from about 10 mg to about 600 mg of the subject compound per dose.

Suitable pharmaceutically-acceptable carriers for topical application include those suited for use in lotions, creams, gels and the like. Topical compositions preferably contain from about 1% to about 50% of an emollient, more preferably from about 5% to about 25% of an emollient. Such topical compositions preferably comprise from about 0.1% to about 50%, of the subject compound, more preferably from 0.5% to about 10%, also preferably from about 5 mg to about 3500 mg per dose.

The preferred mode of administering the subject compound is perorally. The preferred unit dosage form is therefore tablets, capsules and the like, comprising a safe and effective amount of the compound, which is preferably from about 5 mg to about 3500 mg, more preferably from about 10 mg to about 1000 mg, and most preferably from about 25 mg to about 600 mg. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by a person skilled in the art.

Many of the subject compounds are hydrophobic. If it is desired to provide an aqueous-based composition or a composition soluble in or miscible with aqueous media, a solubilizing agent may be included in the composition. Non-limiting examples of such solubilizing agents include polyethylene glycol, propylene glycol, ethanol, and polyoxyethylene (35) castor oil.

Particularly preferred oral composition carriers suitable for compositions of the subject invention are disclosed in U.S. Pat. Nos. 5,189,066 of Kelm & Bruns, issued Feb. 23, 1993, entitled "Pharmaceutical Compositions of Tebufelone", and 5,281,420 of Kelm & Dobrozsi, issued Jan. 25, 1994, entitled "Solid Dispersion Compositions of Tebufelone", hereby incorporated herein by reference.

Methods

Another aspect of the subject invention is methods for treating or preventing diseases characterized by inflammation by administering a safe and effective amount of a subject compound to a human or lower animal in need of such treatment. The term "diseases characterized by inflammation", as used herein, means conditions which are known to involve inflammation, and may include conditions such as arthritis (e.g., rheumatoid arthritis, osteoarthritis, psoriatic arthritis, juvenile arthritis, Reiter's syndrome, infectious arthritis, and ankylosing spondylitis, systemic lupus, erythematosus and gout), as well as the presence of inflammation whether or not it is associated with an identifiable disease. Diseases characterized by inflammation further may include inflammation in the oral cavity (e.g., inflammation associated with gingivitis or periodontal disease); inflammation in the gastrointestinal tract, (e.g., inflammation associated with ulcers and irritable bowel disease); inflammation associated with dermatological diseases (e.g., psoriasis, acne, and other skin inflammation); inflammation associated with the respiratory tract (e.g., asthma, bronchitis, and allergies); and inflammation in the central nervous system (e.g., Alzheimer's disease).

Another aspect of the subject invention is methods for treating or preventing pain by administering a safe and effective amount of a subject compound to a human or lower animal in need of such treatment. Pain which can be treated or prevented by administering the subject compounds may include peripheral pain, menstrual pain, dental pain, and lower back pain.

Another aspect of the subject invention is methods for preventing oxidative damage at inflammatory sites by administering a safe and effective amount of a subject compound to a human or lower animal in need of such treatment. While not limited to a particular mechanism, it is believed that the subject compounds inhibit leukotriene synthesis, thereby decreasing neutrophil accumulation at an inflammatory site.

Another aspect of the subject invention is methods for treating or preventing gastric or duodental ulcers or erosions by administering a safe and effective amount of a subject compound to a human or lower animal in need of such treatment. In particular, such ulcers or erosions caused by ethanol or non-steroidal antiinflammatory drugs (NSAIDs) can be treated and/or prevented by adminsitration of preferred subject compounds.

Appropriate tests for determining the gastronintestinal safety or gastroprotective or gastric healing properties of the subject compounds are known.

Methods for determining acute gastrointestinal safety are disclosed and/or referred to in the following references: Unangst, P. C., G. P. Shrum, D. T. Connor, R. D. Dyer, and D. J. Schrier, "Novel 1,2,4-Oxadiazoles and 1,2,4-Thiadizoles as Dual 5-Lipoxygenase and cyclooxygenase Inhibitors", *J. Med. Chem.*, Vol. 35 (1992), pp. 3691–3698; and Segawa, Y, O. Ohya, T. Abe, T. Omata, et al., "Anti-inflammatory, Analgesic, and Antipyretic Effects and Gastrointestinal Toxicity of the New Anti-inflammatory Drug N-[3-[3-(piperidinylmethyl)phenoxy]propyl]-carbamoylmethylthio]ethyl 1-(p-chlorobenzoyl) 5-Methoxy-2methyl-3-indolylacetate", *Arzneim.-Forsch./Drug Res.*, Vol. 42 (1992); In the methods disclosed therein, stomachs of the animals are typically examined two hours after dosing a compound. Methods for determining subchronic gastrointestinal safety are disclosed and/or referred to in the following references: Melarange, R., C. Gentry, et al., "Anti-inflammatory and Gastrointestinal Effects of Nabumethone or its Active Matabolite, 6-Methoxy-2-naphthylacetic Acid (6MNA)", *DIG. DIS. Sci.*, Vol. 37 (1992), pp. 1847–1852; and Wong, S. , S. J. Lee, et al., "Antiarthritic Profile of BF-389—a Novel Anti-inflammatory Agent With Low Ulcerogenic Liability", *Agents Actions*, Vol. 37 (1992), pp. 90–91.

Methods for determining acute gastro protection are disclosed and/or referred to in the following reference: Playford, R. J., D. A. Versey, S. Haldane, M. R. Alison, and J. Calan, "Dose-dependent Effects of Fentanyl on Indometharin-induced Gastric Damage", *Digestion*, Vol. 49 (1991), pp. 198–203. In the method disclosed therein, female Lewis rats (130–175 g) are dosed perorally with the subject compound (40 mg/kg b.i.d.) or vehicle at 2 hours and immediately before administration of a gastric damaging does of indomethacin. The rats are sacrificed 4 hours later by $CO_2$ asphyxiation. Gastric corpus damage (millimeters or hemorrhagic lesions) is measured by digitized imaging.

The preferred mode of administration of the subject compounds is peroral, but other known methods of administration are contemplated as well, e.g., dermatomucosally (for example, dermally, rectally and the like), and parenterally (for example, by subcutaneous injection, intramuscular injection, intraarticular injection, intravenous injection and the like). Ocular administration and inhalation are also included. Thus specific modes of administration include, without limitation, peroral, transdermal, mucosal, sublingual, intranasal, intramuscular, intravenous, intraperitoneal, subcutaneous, and topical administration.

Preferred doses of the subject compounds range from about 0.2 mg/kg to about 70 mg/kg, more preferably from about 0.5 mg/kg to about 12 mg/kg. Preferred injectable doses comprise from about 0.1 mg/kg to about 10 mg/kg of the subject compound. Preferred topical doses comprise from about 1 mg/cm$^2$ to about 200 mg/cm$^2$ of the subject compound applied to the skin surface. Preferred peroral doses comprise from about 0.5 mg/kg to about 50 mg/kg, more preferably from about 1 mg/kg to about 20 mg/kg, more preferably still from about 2 mg/kg to about 10 mg/kg, of the subject compound. Such doses are preferably administered from about one to about six times daily, more preferably from about twice to about four times daily. Such daily doses are preferably administered for at least one week, also preferably for at least two weeks, also preferably at least one month, also preferably for at least 2 months, also preferably for at least 6 months, 1 year, 2 years, or more.

Compositions and method Examples

The following non-limiting examples illustrate the subject invention.

EXAMPLE A

Pharmaceutical compositions in the form of tablets are prepared by conventional methods, such as mixing and direct compaction, formulated as follows:

| Ingredient | Quantity (mg per tablet) |
| --- | --- |
| Compound 1 | 200 |
| Microcrystalline Cellulose | 100 |
| Sodium Starch Glycollate | 30 |
| Magnesium Stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

EXAMPLE B

A pharmaceutical composition in capsule from is prepared by conventional methods, formulated as follows:

| Ingredient | Quantity (mg per capsule) |
| --- | --- |
| Compound 2 | 200 |
| Lactose | to fill to volume of capsule |

The above capsule administered orally once a day substantially reduces the symptomology of a patient afflicted with rheumatoid arthritis or osteoarthritis.

EXAMPLE C

A pharmaceutical composition in liquid form is prepared by conventional methods, formulated as follows:

| Ingredient | Quantity |
| --- | --- |
| Compound 4 | 200 mg. |
| EtOH | 4 ml |

17

-continued

| Ingredient | Quantity |
|---|---|
| Methyl cellulose | 0.4 mg |
| Distilled water | 76 ml |
| Tween 80 | 1.6 ml |

50 ml of the above composition administered perorally once a day substantially reduces the symptoms of a patient afflicted with rheumatoid arthritis or osteoarthritis.

EXAMPLE D

A pharmaceutical composition in liquid form is prepared by conventional methods, formulated as follows:

| Ingredient | Quantity |
|---|---|
| Microcrystalline (micronized) Compound 8 | 200 mg |
| Avicel (microcrystalline cellulose) | 50 mg |
| Tween 80 | 1.6 ml |
| Methyl cellulose | 0.4 mg |
| Deionized water | 80 ml |

50 ml of the above composition administered perorally twice a day substantially reduces the symptoms of a patient afflicted with rheumatoid arthritis or osteoarthritis.

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

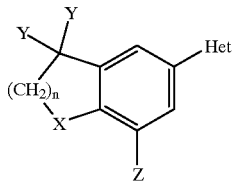

wherein
(a) n is 3;
(b) X is selected from the group consisting of O, S, SO, or $SO_2$;
(c) Y is independently hydrogen or straight, branched or cyclic alkyl having from 1 to about 4 carbon atoms, or the Y's are bonded together to form an alkanyl ring having from about 3 to about 7 atoms;
(d) Z is hydrogen or straight, branched or cyclic alkyl having from 3 to about 10 atoms other than hydrogen, or unsubstituted or alkanyl-substitited phenyl or benzyl, provided that when both Y's are hydrogen, Z is straight, branched or cyclic alkyl having from 3 to about 10 atoms, or unsubstituted or alkanyl-substitited phenyl or benzyl; and
(e) Het is a heteroaryl group comprising one or more rings each ring containing from about 5 to about 6 atoms other than hydrogen and wherein the group contains at least one heteroatom selected from O, N, or S.

18

2. The compound of claim 1 wherein X is oxygen or sulphur.

3. The compound of claim 2 wherein each Y is independently selected from the group consisting of hydrogen, methyl and ethyl; and Z is selected from the group consisting of hydrogen, $C_4$–$C_6$ branched alkanyl having 2 branches, $C_3$–$C_6$ cycloalkanyl, and phenyl.

4. The compound of claim 3 wherein X is oxygen, both Y are methyl, and Z is t-butyl.

5. The compound of claim 3 wherein Het is selected from the group consisting of 2 or 3-furyl, 2 or 3-thienyl, 2 or 3-pyrrolyl either unsubstituted or alkyl substituted on nitrogen, 2, 4, or 5 thiazolyl, 2 or 5-oxazolyl, 2, 4, or 5-imidazolyl either unsubstituted or alkyl-substituted on nitrogen, 3, 4, or 5-isoxazolyl, 3, 4, or 5-isothiazolyl, 3, 4, or 5-pyrazolyl unsubstituted or alkyl-substituted on nitrogen, 2 or 5-oxadiazolyl, 2 or 5-thiadiazolyl, triazolyl, tetrazolyl, pyridyl, pyrimidinyl, or pyrazinyl, imidazothiazolinyl, imidazopyridinyl, imidazoimidazolinyl, indolyl, quinolyl, or isoquinolyl.

6. The compound of claim 5 wherein X is oxygen, and Het is selected from the group consisting of 2-furanyl; 2-thienyl; 2-(5-bromothienyl); 4-thiazolyl; 4-(2-guanidinothiazolyl); 5-methyl-1,2,4-oxadiazolyl, 6-imidazo[2,1,b]thiazolinyl; 1-oxo-6-imidazo[2,1,b]thiazolinyl; or 2-imidazo(1,2a) pyridine.

7. The compound of claim 6 wherein both Y are methyl, and Z is t-butyl.

8. A method of treating inflammation or pain comprising administration, to a human or lower animal in need of such treatment, of a safe and effective amount of a compound having the structure:

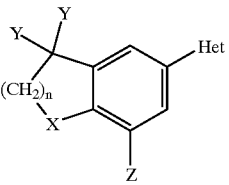

wherein
(a) n is 3;
(b) X is selected from the group consisting of O, S, SO, or $SO_2$;
(c) Y is independently hydrogen or straight, branched or cyclic alkyl having from 1 to about 4 carbon atoms, or the Y's are bonded together to form an alkanyl ring having from about 3 to about 7 atoms;
(d) Z is hydrogen or straight, branched or cyclic alkyl having from 3 to about 10 atoms other than hydrogen, or unsubstituted or alkanyl-substitited phenyl or benzyl; and
(e) Het is a heteroaryl group comprising one or more rings each ring containing from about 5 to about 6 atoms other than hydrogen and wherein the group contains at least one heteroatom selected from O, N, or S.

9. A method of treating arthritis comprising daily peroral administration, to a human in need of such treatment, of from about 1 mg/kg to about 20 mg/kg of a compound having the structure:

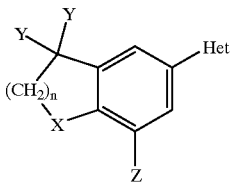

wherein
- (a) n is 3;
- (b) X is selected from the group consisting of O, S, SO, or $SO_2$;
- (c) Y is independently hydrogen or straight, branched or cyclic alkyl having from 1 to about 4 carbon atoms, or they Y's are bonded together to form an alkanyl ring having from about 3 to about 7 atoms;
- (d) Z is hydrogen or straight, branched or cyclic alkyl having from 3 to about 10 atoms other than hydrogen, or unsubstituted or alkanyl-substitited phenyl or benzyl; and
- (e) Het is a heteroaryl group comprising one or more rings each ring containing from about 5 to about 6 atoms other than hydrogen and wherein the group contains at least one heteroatom selected from O, N, or S.

10. A composition comprising a compound of claim 7 and a pharmaceutically-acceptable carrier.

11. A method of treating inflammation or pain comprising administration, to a human or lower animal in need of such treatment, of a safe and effective amount of a compound of claim 7.

12. A method of treating arthritis comprising daily peroral administration, to a human in need of such treatment, of from about 1 mg/kg to about 20 mg/kg of a compound of claim 7.

13. A composition comprising a pharmaceutically-acceptable carrier and a compound having the structure:

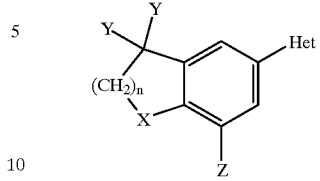

wherein
- (a) n is 3;
- (b) X is selected from the group consisting of O, S, SO, or $SO_2$;
- (c) Y is independently hydrogen or straight, branched or cyclic alkyl having from 1 to about 4 carbon atoms, or the Y's are bonded together to form an alkanyl ring having from about 3 to about 7 atoms;
- (d) Z is hydrogen or straight, branched or cyclic alkyl having from 3 to about 10 atoms other than hydrogen, or unsubstituted or alkanyl-substitited phenyl or benzyl; and
- (e) Het is a heteroaryl group comprising one or more rings each ring containing from about 5 to about 6 atoms other than hydrogen and wherein the group contains at least one heteroatom selected from O, N, or S.

* * * * *